United States Patent [19]
Parsons

[11] Patent Number: 4,749,404
[45] Date of Patent: Jun. 7, 1988

[54] HERBICIDAL LIQUID CONCENTRATE COMPOSITIONS

[75] Inventor: John W. Parsons, Wilmington, Del.

[73] Assignee: American Cyanamid Company, Stamford, Conn.

[21] Appl. No.: 631,284

[22] Filed: Jul. 16, 1984

[51] Int. Cl.[4] ............................................. A01N 43/48
[52] U.S. Cl. .................................. 71/92; 71/DIG. 1; 71/88
[58] Field of Search ........................... 71/92, DIG. 1

[56] References Cited

U.S. PATENT DOCUMENTS 4,400,196 8/1963 Albrecht et al. ............... 71/DIG. 1
4,459,408 7/1984 Maulding et al. ................ 546/167

FOREIGN PATENT DOCUMENTS 0041623 12/1981 European Pat. Off. ............ 71/92

OTHER PUBLICATIONS

Middleton, "Pesticidal Compositions," (11-1983), Chem. Abstr. 100:98315n, (1984).
Hawley, "Condensed Chemical Dictionary", (1983), New York, 10th Ed., pp. 484, 1007.

Primary Examiner—Glennon H. Hollrah
Assistant Examiner—A. A. Owens
Attorney, Agent, or Firm—H. G. Jackson

[57] ABSTRACT

The present invention provides novel herbicidal liquid concentrate compositions of 2-(4-isopropyl-4-methyl-5-oxo-2-imidazolin-2-yl)-3-quinolinecarboxylic acid which exhibit enhanced biological efficacy, that are suitable for preparing combination compositions containing herbicidal 2,6-dinitroaniline which exhibit excellent thermal stability.

2 Claims, No Drawings

HERBICIDAL LIQUID CONCENTRATE COMPOSITIONS

SUMMARY OF THE INVENTION

Herbicidal substituted pyridine and quinoline-2-imidazolin-2-yl acids, esters and salts are discloses in European Patent Application No. 81103638.3.

The above-identified application also described aqueous compositions of the salts of these herbicidal pyridine and quinoline-2-imidazolin-2-yl acids which may simply be dispersed in water and applied as a dilute aqueous spray to the foilage of plants or to soil containing propagating organs thereof.

While the above aqueous compositions are suitable for applying the salts of said pyridine and quinoline compounds, they are not always suitable for the preparation of combination compositions containing other herbicides like the 2,6-dinitroanilines, which are normally applied as aqueous emulsions that are prepared from organic based emulsifiable concentrate compositions. Since the use of herbicidal combinations for the control of undesirable vegetation is a well established practice, it would be desirable to have compositions containing 2-(4-isopropyl-4-methyl-5-oxo-2-imidazolin-2-yl)-3-quinolinecarboxylic acid salts as described in the above-identified patent application, which will disperse well in water when the compound is applied alone and also be suitable for the preparation of stable combination compositions which are organic in nature.

The invention provides novel liquid concentrate compositions of salts of 2-(4-isopropyl-4-methyl-5-oxo-2-imidazolin-2-yl)-3-quinolinecarboxylic acid of the formula:

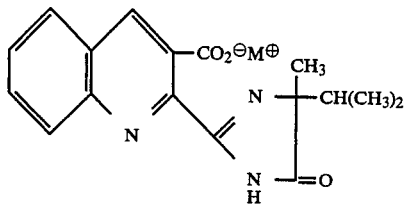

wherein M is sodium, potassium, ammonium or

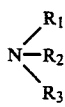

wherein $R_1$, $R_2$ and $R_3$ are $C_1$-$C_{18}$ alkyl or hydrogen, dissolved in $C_1$-$C_{12}$ alcohols, diols or alcohol ethers, which both disperse well in water and provide stable combination compositions with organic based compositions containing herbicidal 2,6-dinitroaniline compounds such as N-(1-ethylpropyl)-2,6-dinitro-3,4-xylidine, (pendiethalin), and α,α,α-trifluoro-2,6-dinitro-N,N-dipropyl-p-toluidine (trifluralin). Additionally, it has been found that the liquid concentrate compositions of the invention containing salts of 2-(4-isopropyl-4-methyl-5-oxo-2-imidazolin-2-yl)-3-quinolinecarboxylic acid as described above dissolved in alcohols such as tetrahydrofurfuryl alcohol exhibit enhanced postemergence herbicidal activity over previously disclosed aqueous compositions.

The compositions of the invention containing the salts of 2-(4-isopropyl-4-methyl-5-oxo-2-imidazolin-2-yl)-3-quinolinecarboxylic acid also provide an improved method for the postemergence control of undesired vegetation in crop plants that require lower rates of application of 3-quinolinecarboxylic acid salts both alone and in combination compositions for the control of undesired vegetation.

The liquid concentrate compositions of the invention may be prepared by adding aqueous or organic base to a slurry of 12% to 50% by weight of 2-(4-isopropyl-4-methyl-5-oxo-2-imidazolin-2-yl)-3-quinolinecarboxylic acid in the desired alcohol, 40% to 80% by weight, in sufficient amounts to obtain a clear solution.

The amount of base added will vary depending upon the amount of alcohol, alcohol ether, or diol and the base used and whether it is aqueous or organic. The amounts most commonly employed are in a range of from 1 to 2.5 molar equivalents, based upon the quinolinecarboxylic acid. Combination compositions may then be prepared with thus-obtained liquid concentrate by simply admixing the desired organic dinitroaniline composition until a homogeneous mixture is obtained, or by adding each of the individual components separately and mixing until homogeneous.

Herbicidal dinitroaniline compositions suitable for incorporation into the combination compositions normally contain 20% to 40% on a weight basis of the dinitroaniline herbicide, 1% to 12% on a weight basis of surfactants and 50% to 79% on a weight basis of an organic solvent, which is normally used for the preparations of these compounds such as xylene, monochlorobenzene or chlorinated hydrocarbons and the like.

Uniquely, it has been found that the liquid concentrate compositions of the invention are suitable for making combination compositions with a wide variety of herbicidal dinitroaniline compositions resulting in combinations which are stable over a wide range of temperatures of from −20° C. to 45° C., and through repeated freeze-thaw cycles.

The invention is further illustrated by the following non-limiting examples.

EXAMPLE 1

Preparation of liquid concentrate composition of the ammonium salt of 2-(4-isopropyl)-4-methyl-5-oxo-2-imidazolin-2-yl)-3-quinolinecarboxylic acid Ammonium hydroxide 16.4 g of a 30% by weight solution of ammonia is added portionwise to a slurry of 2-(4-isopropyl-4-methyl-5-oxo-2-imidazolin-2-yl)-3-quinolinecarboxylic acid, 50 g having a purity of 85.1% in tetrahydrofurfuryl alcohol, 40 g.

The resulting mixture is stirred until homogenous to give a liquid concentrate as a clear solution, which is comprised of 38% by weight of tetrahydrofurfuryl alcohol, 40% by weight of the quinolinecarboxylic acid and 15% by weight of 30% ammonium hydroxide.

EXAMPLE 2

Postemergence herbicidal activity of liquid concentrate compositions

The liquid concentrate composition prepared in Example 1 was evaluated for postemergent herbicidal activity in direct comparison to three other compositions.

Each of the four compositions listed in Table I below is diluted in water to provide 500, 250, 125 and 63 g/ha of active ingredient, to which a nonionic surfactant, polyoxyethylene sorbitan monolaurate (TWEEN 20 ®) 0.125% (v/v) is added.

Seeds of the test species (Table II) are planted in the upper 1.25 cm of a loamy sand soil (5.0% O.M.) contained in 161 cm² fiber pots. The plants are allowed to grow in the greenhouse for two weeks prior to treatment. At treatment time, soybeans are at the V2 stage of growth and weeds were in the 2- to 4-leaf stage of growth.

Each treatment is replicated two times. A belt sprayer is used to deliver a volume equivalent to 281 L/ha. Plants are allowed to grow in the greenhouse following treatment. Evaluations are made at 5 DAT for soybean phytotoxicity and again at 5 WAT for weed control and soybean phytotoxicity.

Soybean phytotoxicity and weed control are evaluated and expressed on a 0 to 9 rating scale (0=no effect, 9=complete control), where ≧8 is effective weed control and ≦2 is good crop tolerance (as indicated in the herbicide rating scale below). Results of the weed control are summarized as effective rates for control.

Herbicide Rating Scale

| Rating | Meaning | % Control (Compared to Check) |
|---|---|---|
| 9 | Complete kill | 100 |
| 8 | Approaching complete kill | 91–99 |
| 7 | Good herbicidal effect | 80–90 |
| 6 | Herbicidal effect | 65–79 |
| 5 | Definite injury | 45–64 |
| 4 | Injury | 30–44 |
| 3 | Moderate effect | 16–29 |
| 2 | Slight effect | 6–15 |
| 1 | Trace effect | 1–5 |
| 0 | No effect | 0 |

TABLE I

Compositions Tested

| | |
|---|---|
| Dispersible granule (80 DG) | 80.1% active ingredient obtained by admixing |
| | i. 90% on a weight basis of 2-(4-isopropyl-4-methyl-5-oxo-2-imidazolin-2-yl)-3-quinolinecarboxylic acid (88.4% pure) with |
| | ii. 8% on a weight basis of a sodium naphthaleneformaldehyde condensate and |
| | iii. 2% on a weight basis of sodium salt of sulfated alkyl carboxylate and sulfonated alkyl naphthalene, yields the chemically and physically stable 80 DG. |
| Dispersible granule (75 DG) | 75.0% active ingredient obtained by admixing |
| | i. 87.2% on a weight basis of 2-(4-isopropyl-4-methyl-5-oxo-2-imidazolin-2-yl)-3-quinolinecarboxylic acid (86.0% pure) with |
| | ii. 8% on a weight basis of a sodium naphthaleneformaldehyde condensate and |
| | iii. 2% on a weight basis of a sodium salt of sulfated alkyl carboxylate and sulfonated alkyl naphthalene, and |
| | iv. 2.8% on a weight basis of kaolin yields the chemically and physically stable 75 DG. |
| Aqueous solution of ammonium salt (Ammonium AS) | 20.0% active ingredient |
| Liquid concentrate of the invention (Ammonium LC) | 40.0% active ingredient |

TABLE II

Species Tested

| | |
|---|---|
| Glycine max | Soybeans, cv. Bragg |
| Abutilon theophrasti | Velvetleaf |
| Ipomoea spp. | Morningglory |
| Setaria viridis | Green Foxtail |

The results of these evaluations which are summarized in Table III and Table IV below demonstrate that the liquid concentrate composition of the invention controls the weeds at lower rates of application of active ingredient and retains the selectivity in soybeans at these rates.

TABLE III

Weed control obtained with different compositions

| | Control Rate* | | | |
|---|---|---|---|---|
| Formulation | Morningglory (g/ha) | Velvetleaf (g/ha) | Green foxtail (g/ha) | Avg Weed control rate (g/ha) |
| Ammonium LC + TWEEN 20 ® | 250 | 63 | 63 | 125 |
| Ammonium AS + TWEEN 20 ® | 500 | 125 | 125 | 250 |
| 80 DG + TWEEN 20 ® | 500 | 500 | 125 | 375 |
| 75 DG + TWEEN 20 ® | 500 | 250 | 125 | 292 |

*Average value of two replicates

TABLE IV

Soybean injury ratings* obtained with different compositions

| | 5 DAT | | | | 5 WAT | | | |
|---|---|---|---|---|---|---|---|---|
| Formulation | 500 (g/ha) | 250 (g/ha) | 125 (g/ha) | 63 (g/ha) | 500 (g/ha) | 250 (g/ha) | 125 (g/ha) | 63 (g/ha) |
| Ammonium LC + TWEEN 20 ® | 3.5 | 3.5 | 2.0 | 1.5 | 2.5 | 1.0 | 0.0 | 0.0 |

TABLE IV-continued

| | Soybean injury ratings* obtained with different compositions | | | | | | | |
|---|---|---|---|---|---|---|---|---|
| | 5 DAT | | | | 5 WAT | | | |
| Formulation | 500 (g/ha) | 250 (g/ha) | 125 (g/ha) | 63 (g/ha) | 500 (g/ha) | 250 (g/ha) | 125 (g/ha) | 63 (g/ha) |
| Ammonium AS + TWEEN 20 ® | 3.5 | 2.5 | 2.0 | 1.0 | 2.0 | 0.5 | 0.0 | 0.0 |
| 80 DG + TWEEN 20 ® | 4.0 | 3.0 | 1.5 | 1.0 | 1.0 | 1.0 | 0.5 | 0.0 |
| 75 DG + TWEEN 20 ® | 2.5 | 2.5 | 1.0 | 1.0 | 0.0 | 0.0 | 0.0 | 0.0 |

*Average value of two replicates

EXAMPLE 3

Preparation of combination compositions of salts of 2-(4-isopropyl-4-methyl-5-oxo-2-imidazolin-2-yl)-3-quinolinecarboxylic acids with dinitroaniline herbicides Combination compositions are prepared by first preparing liquid concentrate compositions by the procedure described in Example 1. Representative liquid concentrate compositions suitable for preparing compositions are listed in Table V below.

Combination compositions are then prepared by adding the desired organic solvent, the herbicidal dinitroaniline and surfactants as illustrated in Table V below, wherein monochlorobenzene, 29.45 g, N-(1-ethylpropyl)-2,6-dinitro-3,4-xylidine(pendimethalin), 17.15 g, and a mixture of nonionic mixed polyoxypropylene-/polyoxyethylene surfactants, 3.4 g to 3.84 g and polyoxyethylated castor oil, 2.9 g, is admixed with a liquid concentrate until a homogeneous solution is obtained.

The emulsion properties of the sample is determined by visual inspection of a 2 gram sample diluted to 100 ml with water (SHW and SSW) at ½ and one hour.

The results of these experiments which are summarized in Table VI below, demonstrate that both excellent stability and emulsion properties may be obtained with combination compositions of the invention.

TABLE VI

| | Thermal stability of combination compositions of the invention | | | | | |
|---|---|---|---|---|---|---|
| | Assay % w/w | | | | | |
| | | RT | | 45° C. | | |
| Compound | Initial | 3 mos | 6 mos | 2 mos | 4 mos | 6 mos |
| 2-(4-isopropyl-4-methyl-5-oxo-2-imidazolin-2-yl)-3-quinolinecarboxylic acid | 4.21 | 4.26 | 4.28 | 4.16 | 3.99 | 3.94 |
| N—(1-ethylpropyl)-2,6-dinitro-3,4-xylidine | 25.37 | 25.25 | 25.28 | 25.52 | 25.62 | 25.82 |
| Emulsion Stable | | | | | | |
| One hour SSW | yes | yes | yes | yes | yes | yes |
| One hour SHW | yes | yes | yes | yes | yes | yes |

TABLE V

| | Combination compositions of 2-(4-isopropyl-4-methyl-5-oxo-2-imidazolin-2-yl)-3-quinolinecarboxylic acid salts with herbicidal dinitroanilines | | | | | |
|---|---|---|---|---|---|---|
| | Weight g | | Weight % liquid concentrate | | Weight % combination | |
| Component | 1 | 2 | 1 | 2 | 1 | 2 |
| 2-(4-Isopropyl-4-methyl-5-oxo-2-imidazolin-2-yl)-3-quinolinecarboxylic acid (88.4% ai) | 2.9 | 4.0 | 15.34 | 13.94 | 4.03 (3.6 ai) | 3.91 (3.5 ai) |
| Alcohol | | | | | | |
| a. Tetrahydrofurfuryl | 15.0 | 15.0 | 79.37 | 72.12 | 20.89 | 20.72 |
| Base | | | | | | |
| a. Ammonium hydroxide (30% NH3) | 1.0 | — | 5.29 | | 1.39 | |
| b. Dimethydodecylamine | — | 2.9 | | 13.94 | | 3.91 |
| | Total % | | 100 | 100 | | |
| Dinitroaniline herbicide | | | | | | |
| a. Pendimethalin (93.4%) | 17.15 | 17.15 | — | — | 23.88 | 23.12 |
| Solvent | | | | | | |
| a. Monochlorobenzene | 29.45 | 29.45 | — | — | 41.01 | 39.71 |
| Surfactant | | | | | | |
| a. Nonionic blend of polyoxyropylene and ethylene surfactants (FloMoPHN ®, Desoto, Inc.) | 1.7 | 1.7 | | | 2.36 | 2.29 |
| b. Nonionic blend of polyoxypropylene and ethylene surfactants (FloMoPLA ®, Desoto, Inc.) | 1.7 | 1.7 | | | 2.36 | 2.29 |
| c. Polyoxyethylated castor oil (Emulphor EL 620 ®, GAF) | 2.9 | 2.9 | | | 4.03 | 3.91 |

EXAMPLE 4

Thermal stability of combination compositions of 2-(4-isopropyl-4-methyl-5-oxo-2-imidazolin-2-yl)-3-quinolinecarboxylic acid and N-(1-ethylpropyl)-2,6-dinitro-3,4-xylidine Samples of combination 2 described in Example 3 (20 g of solution) are stored at room temperature and 45° C. At intervals samples are withdrawn and are assayed for active ingredients and their emulsion properties evaluated in both standard hard water, SHW (342 ppm Ca++) and standard soft water, SSW (57 ppm Ca++).

EXAMPLE 5

Freeze-thaw stability of combination compositions

The cold temperature stability of the combination compositions prepared in Example 3 is determined by storing a 20 g sample in a freezer at −20° C. for 15 hours. The samples are then stored at +5° C. in a refrigerator for several hours and inspected visually for solids. Examination of both samples shows that any solids which had formed redissolve readily, without agitation, on standing at +5° C. in from three to six hours indicating the excellent freeze-thaw characteristics of these compositions.

What is claimed is:

1. A liquid concentrate comprising herbicidal salts of 2-(4-isopropyl-4-methyl-5-oxo-2-imidazolin-2-yl)-3-quinolinecarboxylic acid of the formula:

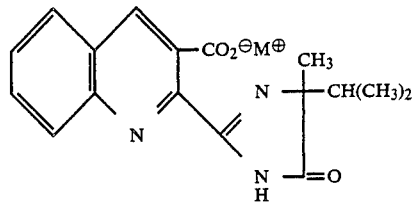

wheren M is sodium, potassium, ammonium or

wherein $R_1$, $R_2$ and $R_3$ are $C_1$–$C_{18}$ alkyl or hydrogen, and 40% to 80% on a weight basis of tetrahydrofurfuryl alcohol.

2. A liquid concentrate composition according to claim 1, wherein M is ammonium.

* * * * *